(12) United States Patent
Wooh (10) Patent No.: US 6,715,354 B2
(45) Date of Patent: *Apr. 6, 2004

(54) FLAW DETECTION SYSTEM USING ACOUSTIC DOPPLER EFFECT

(75) Inventor: Shi-Chang Wooh, Bedford, MA (US)

(73) Assignee: Massachusetts Institute of Technology, Cambridge, MA (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/028,536

(22) Filed: Feb. 24, 1998

(65) Prior Publication Data

US 2001/0015104 A1 Aug. 23, 2001

(51) Int. Cl.[7] .............................................. G01N 29/04
(52) U.S. Cl. ....................................................... 73/598
(58) Field of Search ........................ 73/596, 597, 598, 73/618, 632, 633, 635, 636, 659, 643, 653, 599, 600, 602, 655, 657; 356/345, 352, 357, 358, 445

(56) References Cited

U.S. PATENT DOCUMENTS

| | | | |
|---|---|---|---|
| 3,564,488 A | 2/1971 | Higashi et al. ................. 340/1 |
| 3,812,708 A | 5/1974 | Cowan et al. ............ 73/67.5 R |
| 3,829,827 A | 8/1974 | Ernvein | |
| 3,937,068 A | 2/1976 | Joy ............................ 73/67.7 |
| 3,962,908 A | 6/1976 | Joy ............................ 73/67.7 |
| 3,978,713 A | 9/1976 | Penney | |
| 4,004,455 A | 1/1977 | McKee et al. ................ 73/67.9 |
| 4,127,035 A | 11/1978 | Vasile | |
| 4,143,553 A | 3/1979 | Martens et al. ................ 73/625 |
| 4,174,636 A | 11/1979 | Pagano ......................... 73/636 |
| 4,248,092 A | 2/1981 | Vasile et al. | |
| 4,338,822 A | 7/1982 | Yamaguchi et al. | |
| 4,354,388 A | 10/1982 | Diepers et al. | |
| 4,372,163 A | 2/1983 | Tittmann et al. | |
| 4,435,984 A | 3/1984 | Gruber | |
| 4,437,031 A | 3/1984 | Gunshor et al. | |
| 4,481,822 A | 11/1984 | Kubota et al. | |
| 4,487,071 A | 12/1984 | Pagano et al. ................. 73/612 |
| 4,497,210 A | 2/1985 | Uchida et al. | |
| 4,512,197 A | 4/1985 | von Gutfeld et al. | |
| 4,523,469 A | 6/1985 | Scott et al. | |
| 4,541,280 A | 9/1985 | Cielo et al. | |
| 4,567,769 A | 2/1986 | Barkhoudarian | |
| 4,570,487 A | 2/1986 | Gruber | |
| 4,619,529 A * | 10/1986 | Iuchi et al. .................. 356/358 |
| 4,633,715 A * | 1/1987 | Monchalin .................... 73/657 |

(List continued on next page.)

FOREIGN PATENT DOCUMENTS

| | | |
|---|---|---|
| EP | 0 935 258 A1 | 8/1999 |
| GB | 2008756 B | 6/1979 |
| GB | 2164220 B | 3/1988 |
| JP | 4-64350 A | 2/1992 |
| WO | WO 96/12951 | 5/1996 |
| WO | WO 96/22527 | 7/1996 |
| WO | WO 99/44029 A1 | 9/1999 |

OTHER PUBLICATIONS

U.S. patent application Ser. No. 09/505,039, Wooh, filed Feb. 16, 2000.

Primary Examiner—Richard A. Moller
(74) Attorney, Agent, or Firm—Iandiorio & Teska (57) ABSTRACT

A flaw detection system using acoustic Doppler effect for detecting flaws in a medium wherein there is relative motion between the medium and system includes a transducer, spaced from the medium to be inspected, for introducing to and sensing from the medium an acoustic signal that propagates in the medium at a predetermined frequency; and a detector, responsive to the sensed propagating acoustic signal, for detecting in the sensed acoustic signal the Doppler shifted frequency representative of a flaw in the medium.

15 Claims, 5 Drawing Sheets

U.S. PATENT DOCUMENTS

| | | | |
|---|---|---|---|
| 4,659,224 A | * 4/1987 | Monchalin | 356/352 |
| 4,688,429 A | 8/1987 | Holroyd | |
| 4,700,574 A | 10/1987 | Turbe | 73/636 |
| 4,785,667 A | 11/1988 | Miyajima et al. | |
| 4,821,575 A | 4/1989 | Fujikake et al. | |
| 4,834,111 A | * 5/1989 | Khanna et al. | 128/774 |
| 4,866,614 A | 9/1989 | Tam | |
| 4,932,618 A | 6/1990 | Davenport et al. | 246/122 R |
| 5,035,144 A | 7/1991 | Aussel | |
| 5,079,070 A | 1/1992 | Chalco et al. | |
| 5,125,108 A | 6/1992 | Talwar | |
| 5,129,262 A | 7/1992 | White et al. | |
| 5,152,010 A | 9/1992 | Talwar | |
| 5,154,081 A | 10/1992 | Thompson et al. | |
| 5,172,343 A | 12/1992 | O'Donnell | |
| 5,212,988 A | 5/1993 | White et al. | |
| 5,257,544 A | 11/1993 | Khuri-Yakub et al. | |
| 5,265,831 A | 11/1993 | Muller | 246/124 |
| 5,303,240 A | 4/1994 | Borras et al. | |
| 5,341,683 A | 8/1994 | Searle | 73/597 |
| 5,353,512 A | 10/1994 | Theurer et al. | |
| 5,386,727 A | 2/1995 | Searle | 73/602 |
| 5,402,235 A | 3/1995 | Monchalin | |
| 5,419,196 A | 5/1995 | Havira et al. | 73/636 |
| 5,438,872 A | 8/1995 | Kobayashi et al. | |
| 5,439,157 A | * 8/1995 | Geier et al. | 228/9 |
| 5,457,997 A | * 10/1995 | Naruo et al. | 73/643 |
| 5,488,737 A | 1/1996 | Harbin et al. | |
| 5,522,265 A | 6/1996 | Jaeggi | 73/625 |
| 5,532,697 A | 7/1996 | Hidaka et al. | 342/104 |
| 5,549,003 A | 8/1996 | Drescher-Krasicka | |
| 5,574,224 A | 11/1996 | Jaeggi | 73/636 |
| 5,574,989 A | 11/1996 | Watson et al. | |
| 5,578,758 A | 11/1996 | Havira et al. | 73/636 |
| 5,606,256 A | 2/1997 | Takei | 324/207.21 |
| 5,608,166 A | 3/1997 | Monchalin et al. | |
| 5,627,508 A | 5/1997 | Cooper et al. | 340/425.5 |
| 5,629,485 A | 5/1997 | Rose et al. | |
| 5,634,936 A | 6/1997 | Linden et al. | |
| 5,646,350 A | * 7/1997 | Robinson et al. | 73/602 |
| 5,650,852 A | 7/1997 | Chastain et al. | 356/383 |
| 5,665,907 A | * 9/1997 | Sheen et al. | 73/159 |
| 5,671,154 A | * 9/1997 | Iizuka et al. | 364/507 |
| 5,672,830 A | * 9/1997 | Rogers et al. | 73/597 |
| 5,684,592 A | 11/1997 | Mitchell et al. | |
| 5,698,787 A | 12/1997 | Parzuchowski et al. | |
| 5,724,138 A | 3/1998 | Reich et al. | |
| 5,760,307 A | * 6/1998 | Latimer et al. | 73/643 |
| 5,760,904 A | 6/1998 | Lorraine et al. | |
| 5,763,785 A | 6/1998 | Chiang | |
| 5,767,410 A | 6/1998 | Lareau et al. | |
| 5,801,312 A | 9/1998 | Lorraine et al. | |
| 5,804,727 A | * 9/1998 | Lu et al. | 73/597 |
| 5,808,199 A | * 9/1998 | Kazys et al. | 73/597 |
| 5,814,730 A | * 9/1998 | Brodeur et al. | 73/597 |
| 5,814,732 A | * 9/1998 | Nogami | 73/657 |
| 5,818,592 A | * 10/1998 | Womack et al. | 356/357 |
| 5,824,908 A | * 10/1998 | Schindel et al. | 73/632 |
| 5,827,188 A | 10/1998 | Wright et al. | |
| 5,926,503 A | 7/1999 | Kelton et al. | |
| 5,930,293 A | 7/1999 | Light et al. | |
| 6,061,533 A | 5/2000 | Kajiwara | |
| 6,067,391 A | 5/2000 | Land | |
| 6,078,788 A | 6/2000 | Haardt | |
| 6,092,420 A | 7/2000 | Kimura et al. | |
| 6,128,092 A | 10/2000 | Levesque et al. | |
| 6,186,004 B1 | 2/2001 | Kaduchak et al. | |
| 6,253,618 B1 | 7/2001 | Wooh | |
| 6,324,912 B1 | 12/2001 | Wooh | |
| 6,351,586 B1 | 2/2002 | Krol et al. | |
| 6,360,609 B1 | 3/2002 | Wooh | |
| 6,382,028 B1 | 5/2002 | Wooh et al. | |
| 2002/0108445 A1 | 8/2002 | Wooh | |

* cited by examiner

FLAW DETECTION SYSTEM USING ACOUSTIC DOPPLER EFFECT

FIELD OF INVENTION

This invention relates to a flaw detection system using acoustic Doppler effect for detecting flaws in a medium to be inspected wherein there is relative motion between the system and medium.

BACKGROUND OF INVENTION

Railroads provide both efficiency and economy in passenger and freight transportation. Like other transportation modes, however, they are prone to various problems. Statistics show that over the course of this century, the average carload and trainload tonnage has increased significantly. There is also an increasing concentration of traffic on fewer main line tracks. The average length of haul has also risen. Unfortunately, these trends have not been offset with a proportional increase in the amount of new rail laid. Consequently, the stress on rails and fatigue related failures may continue to increase. With the new demands, it is important to assess the rail integrity by detecting rail defects nondestructively and speedily.

Typical defects often found in railroad tracks include transverse and longitudinal defects in the rail head, web defects, base defects, surface defects as well as other miscellaneous damage such as head wear, corrosion, crushed head, burned rail, bolt hole cracks, head and web separation.

Nondestructive evaluation of rail tracks may be approached by continuous monitoring or detailed inspection. In the context of rail assessment, continuous monitoring results in global evaluation of the rail whereas detailed inspection focuses on a particular area to locate and/or characterize a defect in detail.

In continuous monitoring, some techniques for inspection of rail flaws at an intermediate speed are currently available, but the technology lacks efficient monitoring techniques at a high speed comparable to the speed of a passenger car. One of the limitations on speed is the need for the transducer to be in contact with the rail. Furthermore, existing detailed inspection techniques have limited capabilities, primarily due to poor sensor performance and the requirement of contact with the rail surface.

Currently, surface defects are detected by means of a device called a track circuit. This device uses the track as part of an electric circuit and uses the resistivity of the rail as an indication of surface discontinuities. Another approach is the use of ultrasonic probes in contact with the track surface by a rolling wheel. These techniques require contact with the sensor and the rail. Therefore, they are not quite suitable for high-speed monitoring.

Improved inspection systems are needed in many other applications, for example, in which there is relative motion between the system and medium to be inspected such as conveyors, cables, ropes and roadbeds. Presently inspection techniques tend to be slow and not so reliable because they typically use a change in the amplitude of the probe signal to identify a defect or flaw. Amplitude data is not easily repeatable or reliable.

SUMMARY OF INVENTION

It is therefore an object of this invention to provide a flaw detection system using acoustic Doppler effect for detecting flaws in a medium to be inspected.

It is a further object of this invention to provide such a flaw detection system using acoustic Doppler effect which is faster and more reliable.

It is a further object of this invention to provide such a flaw detection system using acoustic Doppler effect which is adapted for detecting flaws in a variety of moving and stationery mediums such as conveyors, cables, ropes, railroad tracks and roads.

It is a further object of this invention to provide such a flaw detection system using acoustic Doppler effect which utilizes a change in frequency not amplitude to identify a flaw.

It is a further object of this invention to provide such a flaw detection system using acoustic Doppler effect which is capable of extremely high speed operation and improves its resolution with speed.

It is a further object of this invention to provide such a flaw detection system using acoustic Doppler effect which operates in a remote or non-contact mode spaced from the medium to be inspected.

It is a further object of this invention to provide such a flaw detection system using acoustic Doppler effect which can be used to detect surface or internal flaws.

It is a further object of this invention to provide such a flaw detection system using acoustic Doppler effect in which stronger signals can be obtained in surface flaw inspection due to air coupling of acoustic signals.

It is a further object of this invention to provide such a flaw detection system using acoustic Doppler effect which enables continuous non-stop monitoring.

The invention results from the realization that a truly elegant yet extremely reliable continuous and high speed detection system for detecting a flaw in a medium such as a conveyor belt, cable, rope, railroad track or road can be effected by sensing a Doppler shift in a carrier signal caused by a flaw.

This invention features a flaw detection system using acoustic Doppler effect for detecting flaws in a medium wherein there is relative motion between the medium and system. There are transducer means, spaced from the medium to be inspected, for introducing to and sensing from the medium an acoustic signal that propagates in said medium at a predetermined frequency. There are also means, responsive to the sensed propagating acoustic signal, for detecting in the sensed acoustic signal the Doppler shifted frequency representative of a flaw in the medium.

In a preferred embodiment the transducer means may include a separate transmitter and receiver. The transducer may be an ultrasonic transducer and the acoustic signal an ultrasonic signal. The transducer may transmit an acoustic signal from propagation in the medium or the transducer may transmit optical energy for inducing the acoustic signal in the medium. The transducer may include a laser for transmitting that optical energy. The transducer may include an acoustic receiver. The transducer may include an electromagnetic acoustic transmitter and receiver for inducing an acoustic signal into the medium and sensing the Doppler shifted acoustic signal. The means for detecting may include a spectrum analyzer, or a bandpass filter and a peak detector, or an A to D converter and a digital filter for the purpose of distinguishing the Doppler effect frequency. In addition there may be a thresholding circuit identified with any one of the options for identifying a preselected label as a flaw. The medium to be inspected may be a railroad rail. The transducer may transmit to the surface of the medium and receive from the surface of the medium an acoustic signal and the flaws detected may be surface flaws. Or the transmitter may induce an acoustic signal internally in the medium and the flaws detected may be internal flaws. The transducer means may include a laser vibrometer interferometer for sensing the acoustic signal propagating in the medium.

The invention also features a flaw detection system using acoustic Doppler effect for detecting surface flaws when there is relative motion between the medium and system. There is an acoustic transducer means spaced from the medium to be inspected for transmitting an acoustic signal to and receiving the reflected acoustic signal at a predetermined frequency from the surface of the medium to be inspected. Means responsive to the reflected acoustic signal distinguish the Doppler shifted frequency in the reflected acoustic signal from the predetermined frequency of the transmitted acoustic signal representative of a surface flaw in the medium.

The invention also features a flaw detection system using acoustic Doppler effect for detecting flaws in a medium wherein there is relative motion between the medium and system. There are transducer means spaced from the medium to be inspected for inducing an acoustic signal to propagate the medium at a predetermined frequency and sensing the propagated acoustic signal in the medium. Means, responsive to the sensed propagating acoustic signal, distinguish the Doppler shifted frequency representative of a flaw in the medium.

In a preferred embodiment the transducer means may include an electromagnetic acoustic transducer for inducing and sensing the acoustic signal. The transducer means may include a transmitter and a receiver and the transmitter may include a laser for locally heating the medium to generate acoustic signals.

DISCLOSURE OF PREFERRED EMBODIMENT

Other objects, features and advantages will occur to those skilled in the art from the following description of a preferred embodiment and the accompanying drawings, in which.

An advantageous feature of the high-speed flaw detection system using acoustic Doppler effect according to this invention is that the transducer need not, and in fact preferably is not, in contact with the rail or other medium to be inspected. Instead, the transducer remotely senses the discontinuities through the air. There are several devices that operate in a non-contact mode including electromagnetic acoustic transducers (EMAT) (G. A. Alers, *Railroad Rail Flaw Detection System Based on Electromagnetic Acoustic Transducers,* U.S. Department of Transportation Report DOT/FRA/ORD-88-09 (1988) and laser-based acoustic or ultrasound (LBU) (C. B. Scruby and L. E. Drain, *Laser-Ultrasonics: Techniques and Applications,* Adam Hilger, Briston, UK (1990)). More recently, air-coupled piezoelectric transducers have shown interesting results in some materials (A. Safaeinili, O. I. Lobkis, nd D. E. Chimenti, "Air-coupled Ultrasonic Characterization of Composite Plates", *Materials Evaluation,* Vol. 53, 1186–1190 (October 1995)). Air-coupled transducers are attractive because they allow ultrasound to propagate through gaseous media without requiring mechanical contact between the transducer and the medium to be inspected. When used for inspecting railroad tracks the acoustic impedance mismatch between the steel and air is used to great advantage since it reflects most of the energy from the steel surface back to the transducer. When the invention is employed in railroad rail monitoring, a typical car speed for monitoring the rail may reach above sixty miles per hour and in fact, increased car speed leads to more pronounced Doppler effects and better overall efficiency.

Figure 1:
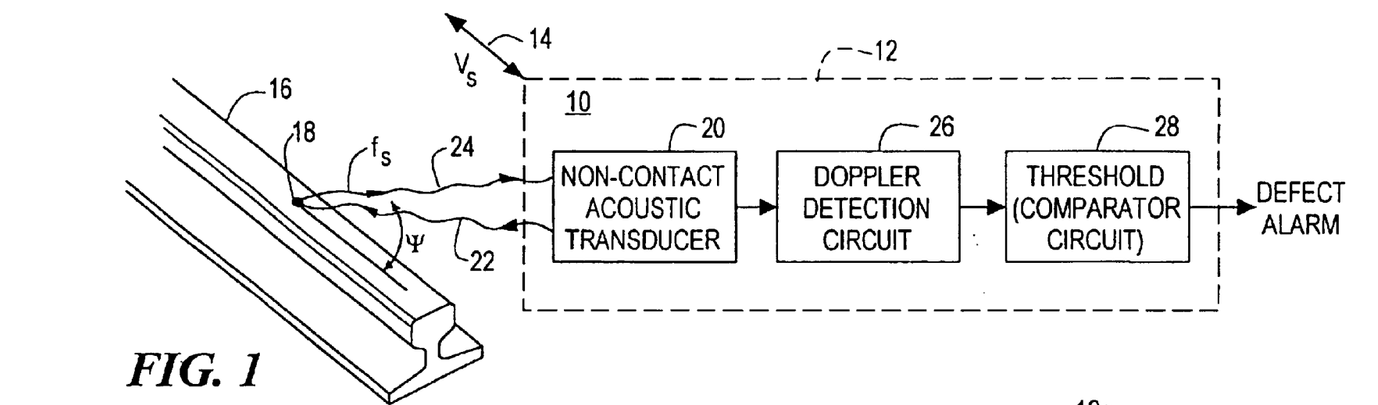
FIG. 1 is a schematic block diagram of a flaw detection system using acoustic Doppler effect detection system according to this invention adapted to inspect for defects in a railroad rail.

There is shown in FIG. 1 a flaw detection system using acoustic Doppler effect system 10 according to this invention mounted on a railroad car 12, indicated generally in phantom, which moves in either direction as indicated by arrow 14 along railroad rail 16, which contains a flaw 18 on its surface. System 10 includes a non-contact acoustic transducer 20 which beams out an acoustic signal 22, referred to as a carrier signal, which reflects back from rail 16 as the returned or reflected signal 24. When signal 22 strikes the smooth portion of rail 16 the carrier signal comes back with its frequency unchanged, but when acoustic signal 22 strikes flaw 18 the return signal 24 will contain Doppler shifted frequency. Depending upon the position of the moving vehicle 12 and/or the direction of the acoustic signal output 22, the Doppler shift may be an increase or a decrease in frequency. The return acoustic signal 24 is sensed and transduced to an electric signal and submitted to Doppler detection circuit 26 which extracts the Doppler frequency and then submits it to a threshold or comparator circuit 28. If the Doppler frequency is above a preselected reference level a defect alarm output is provided by threshold circuit 28.

When a transmitter and receiver are used in a bistatic arrangement, i.e., the transmitter and receiver are separated by a distance and if the angles between the transducers and the target (flaw) are ψ, the Doppler frequency shift can be expressed as:

$$\Delta f = \pm 2 f_s \left(\frac{V_s}{C}\right) \cos \psi \quad (1)$$

where $f_s$ is the frequency of the input signal, $\Delta f$ is the difference between the input frequency and the Doppler shifted frequency, $v_s$ is the relative speed between the system and the medium to be inspected, in this case for example it may be the railroad car carrying the system traveling at for example sixty miles an hour, c is the wave speed in the medium, air in this case, and ψ is the angle between the direction of motion and the direction to the receiving transducer from the notch.

Figure 2:
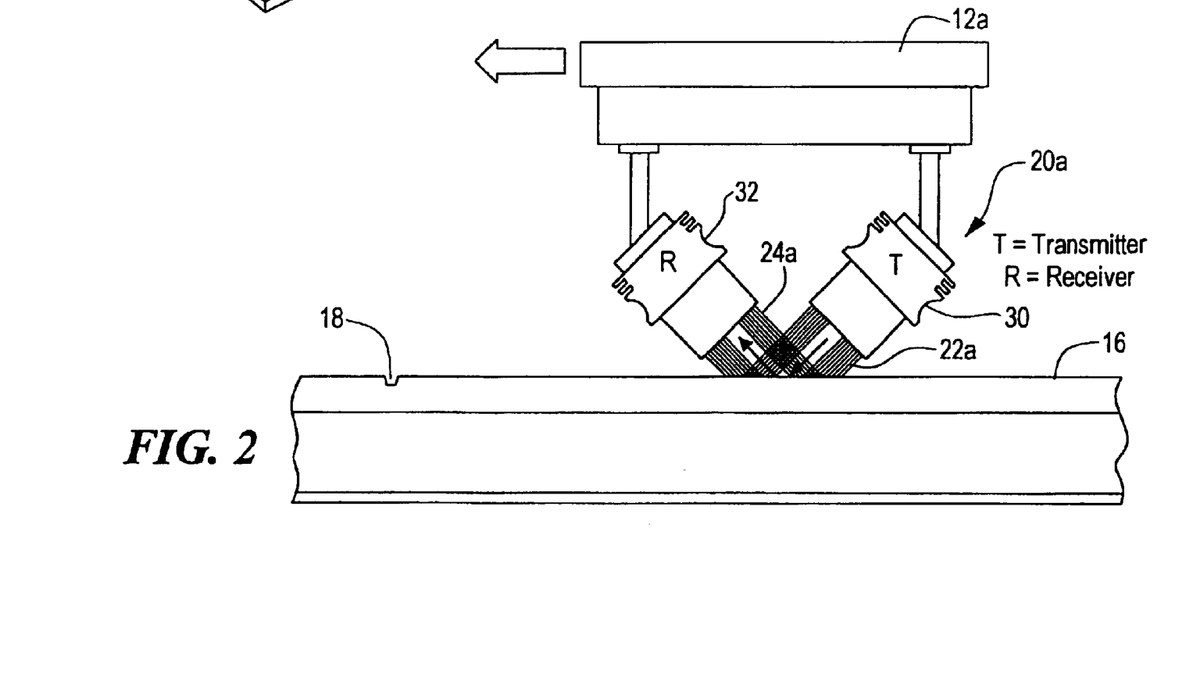
FIG. 2 is an enlarged detailed view of the acoustic transducer of FIG. 1 implemented with separate receiver and transmitter in the ultrasonic range.

Acoustic transducer 20 may be a single transducer which acts as both transmitter and receiver, or it may be two separate units, one a transmitter, the other a receiver. In FIG. 2 transducer 20a includes such discrete devices where a transmitter 30 transmits an ultrasonic output beam 22a and ultrasonic receiver 32 receives the reflected ultrasonic signal 24a.

Figure 3:
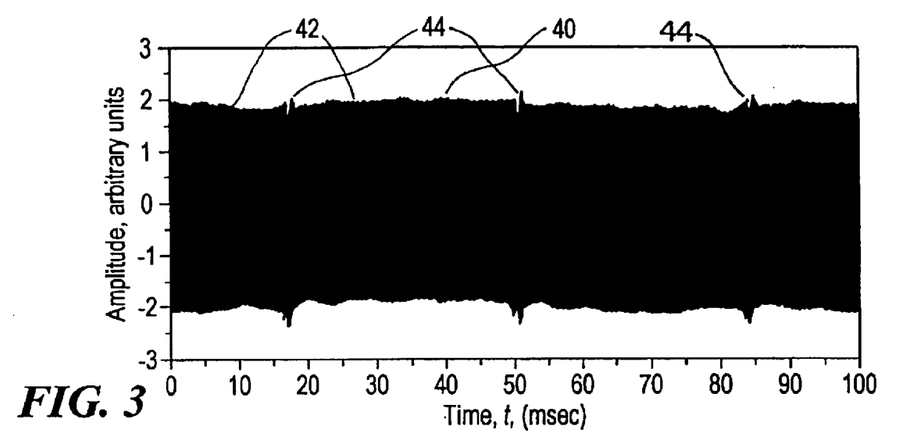
FIG. 3 illustrates the output signal from the acoustic transducer.
Figure 4A:
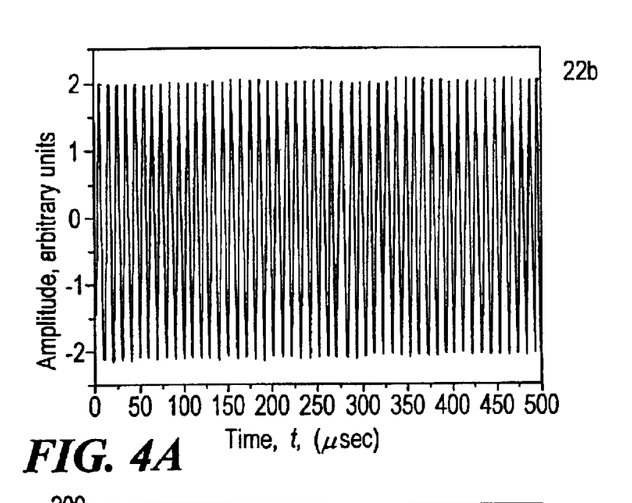
FIG. 4A illustrates the output carrier signal reflected from the unflawed surface.
Figure 4B:
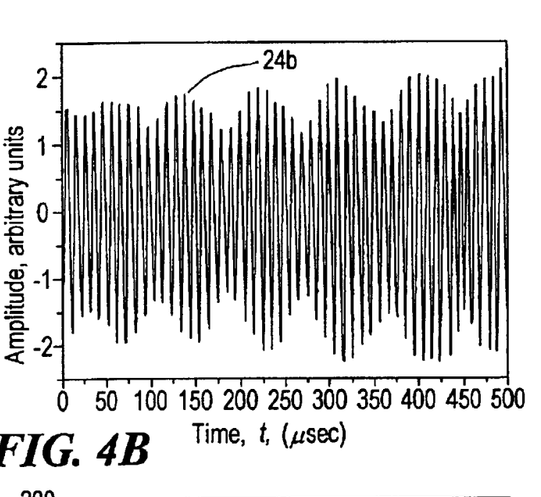
FIG. 4B illustrates the Doppler shifted return signal reflected from a surface flaw.
Figure 4C:
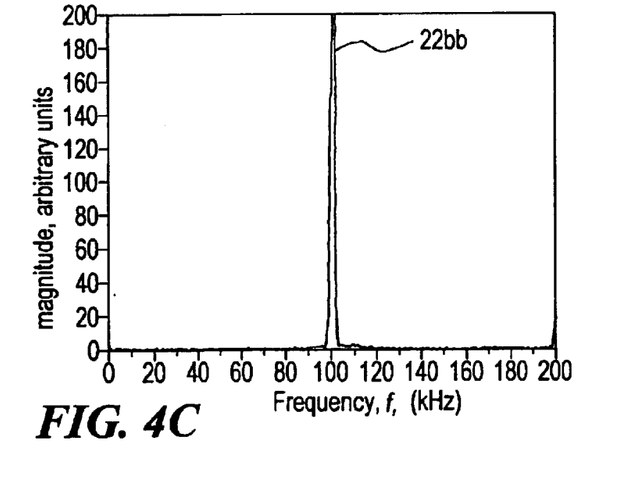
FIG. 4C is the magnitude spectrum of the signal reflected from the unflawed surface.
Figure 4D:
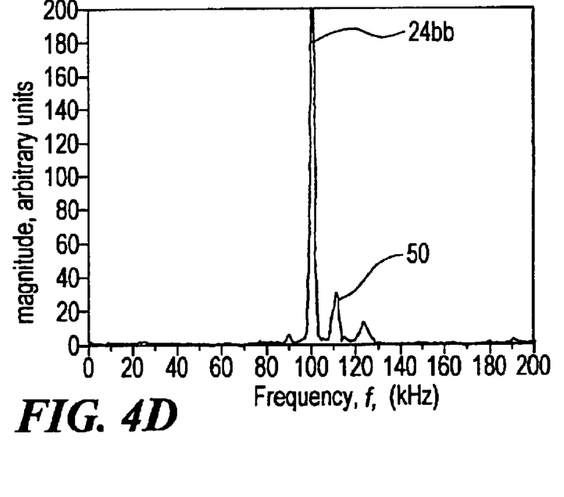
FIG. 4D is the magnitude spectrum of the reflection from the flaw.

The output 40, FIG. 3, of transducer 20 shows a general smooth amplitude profile over time in the areas 42 but shows distinctive characteristics 44 where a defect such as defect 18 has been seen. Typically the output acoustic signal 22b, FIG. 4A, is in the range of 100 kHz. Upon hitting a defect or flaw the return wave appears as at 24b in FIG. 4B. The magnitude spectrum 22bb, FIG. 4C, of output signal 22b shows a marked rise at 100 kHz while the magnitude spectrum 24bb, FIG. 4D for the return signal 24b is accompanied by a very distinct peak 50 at about 115 kHz which is the Doppler shifted frequency resulting from the Doppler effect caused by the flaw 18.

Figure 5:
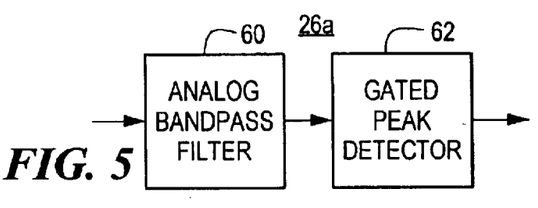
FIG. 5 is a more detailed block diagram of one implementation of the Doppler detection circuit of FIG. 1.
Figure 6:
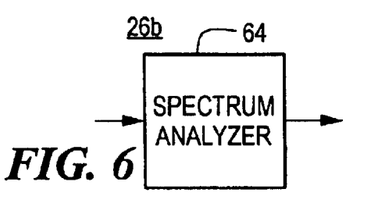
FIG. 6 is a more detailed block diagram of another implementation of the Doppler detection circuit of FIG. 1.

Doppler detection circuit 26 may be implemented in any number of ways. For example, detection circuit 26a, FIG. 5, may include an analog bandpass filter 60 which provides a bandpass window centered on 115 kHz where the Doppler shift is expected at a relative speed of 60 miles an hour between the medium and system. The output from filter 60 is then selected by gated peak detector 62 so that any signals appearing in that band above a certain level will be accepted as a flaw detection. Alternatively, Doppler detection circuit 26b, FIG. 6, may include a spectrum analyzer 64 which directly provides the Doppler shifted frequency output.

Figure 7:
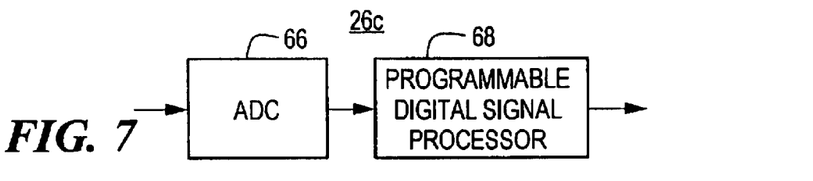
FIG. 7 is a more detailed block diagram of another implementation of the Doppler detection circuit of FIG. 1.
Figure 8:
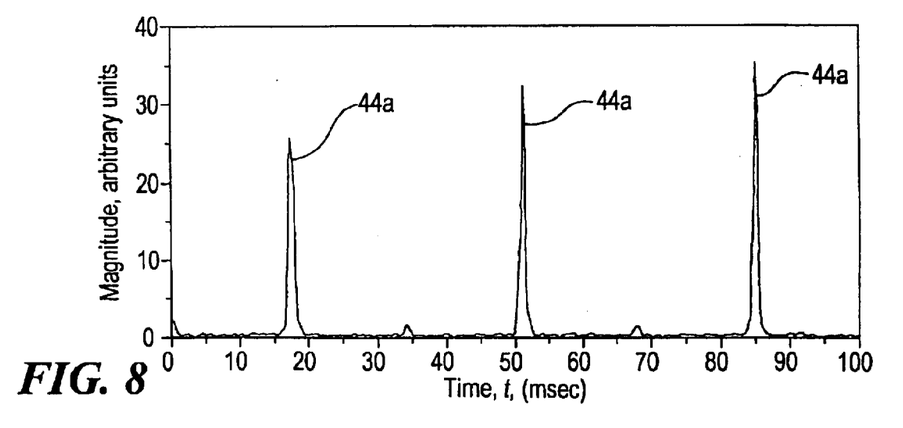
FIG. 8 illustrates the peak magnitude of a Short Time Fourier Transform implementation of the programmable digital signal processor of FIG. 7.

In another implementation 26c, FIG. 7, Doppler detection circuit 26 may include an analog to digital converter 66 which converts the analog signal to a digital signal and then submits it to a programmable digital signal processor 68. The programmable digital signal processor may be programmed in a number of different ways. For example, it may be programmed to operate as a Short-Time Fourier transform. Beginning with the signal as shown in FIG. 3, the Short-Time Fourier Transform $$S_\lambda(f) = \frac{1}{2\pi} \int_{-\infty}^{+\infty} s(t) e^{-i(2\pi f t)} W_\lambda(t) dt \quad (2)$$

results in discrete and prominent features 44a, FIG. 8, corresponding to each of the flaws or defects 44 in FIG. 3.

Figure 9A:
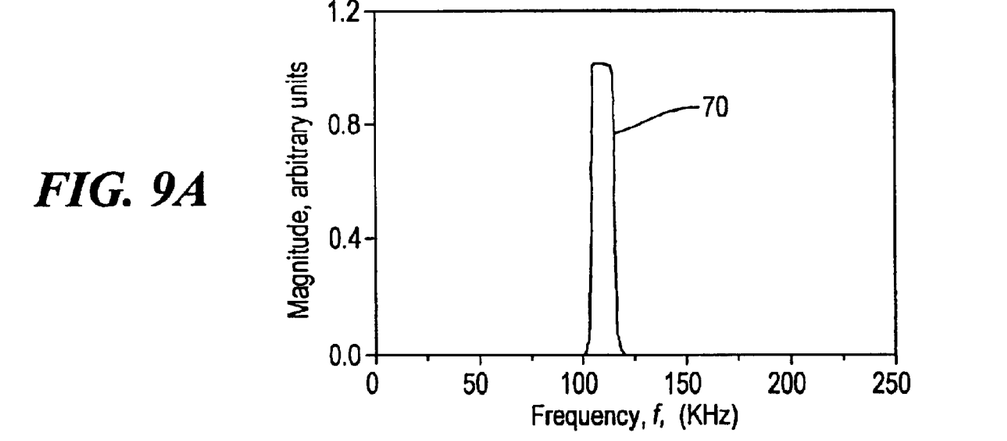
FIG. 9A illustrates the magnitude spectrum of the Doppler window.
Figure 9B:
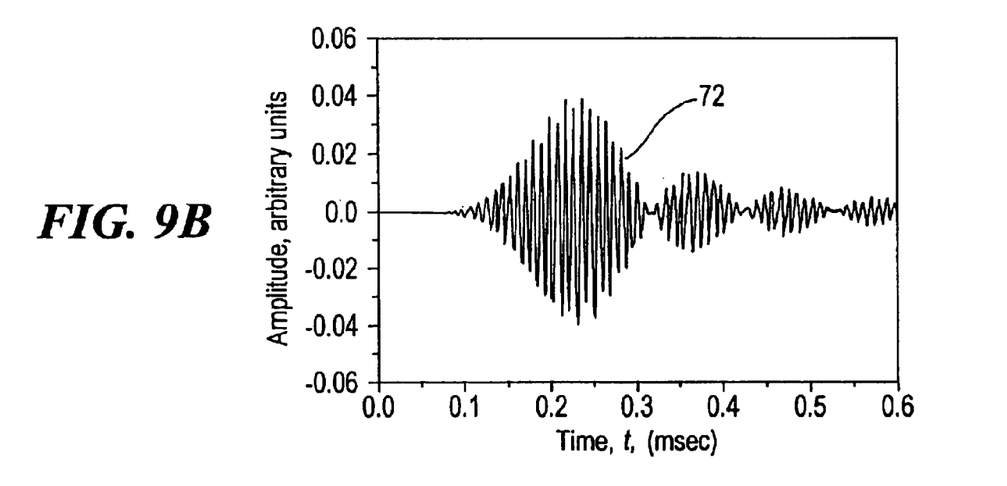
FIG. 9B illustrates the inverse Fourier transform of the magnitude spectrum of FIG. 9A.
Figure 9C:
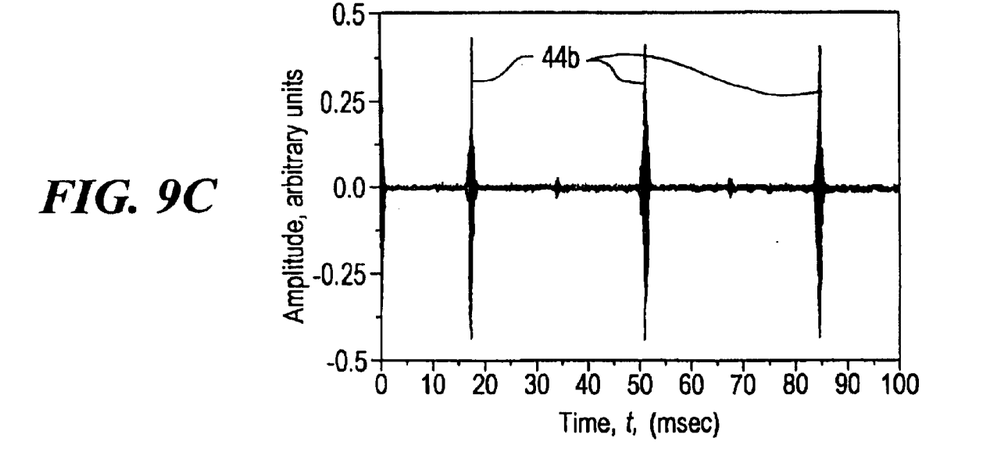
FIG. 9C is the result of convoluting the inverse Fourier transform of FIG. 9B with the input signal of FIG. 3.

Alternatively, the programmable digital signal processor 68 may be programmed to produce a bandpass 70, FIG. 9A, in the range of 105 to 115 kHz then obtain the inverse transform 72, FIG. 9B, of response 70 and convolve it with the return or reflected signal as shown in FIG. 3 in accordance with the input signal designated x (n) and the filter coefficient h (n) in the discrete-time domain directly as shown in the following expression:

$$y(n) = \sum_{k=0}^{N-1} h(k) \times (n-k) \quad (3)$$

wherein y is the filtered output signal, N is the number of points, h is the filter coefficient, k and n are index variables, and x is the input signal. The result of that convolution is shown in FIG. 9C wherein each of the flaws or defects 44, FIG. 3, creates a discrete and very prominent feature 44b.

Figure 10A:
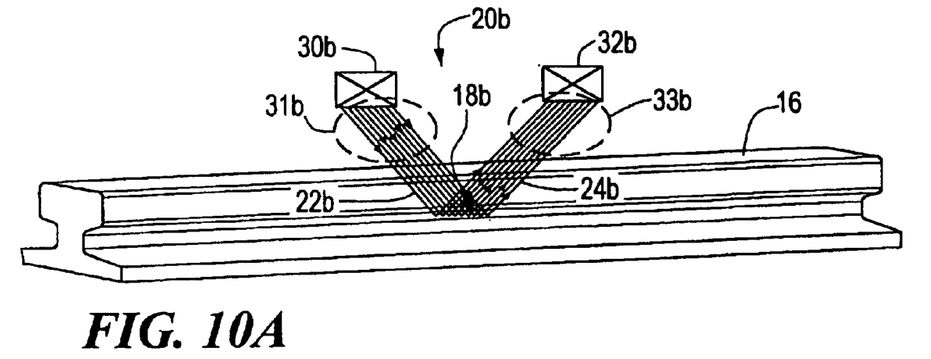
FIGS. 10A, B and C are schematic diagrams showing the acoustic transducer implemented with an electromagnetic acoustic transducer using separate spaced transmitter and receiver, separate adjacent transmitter and receiver, and a single combined transmitter/receiver unit, respectively.
Figure 10B:
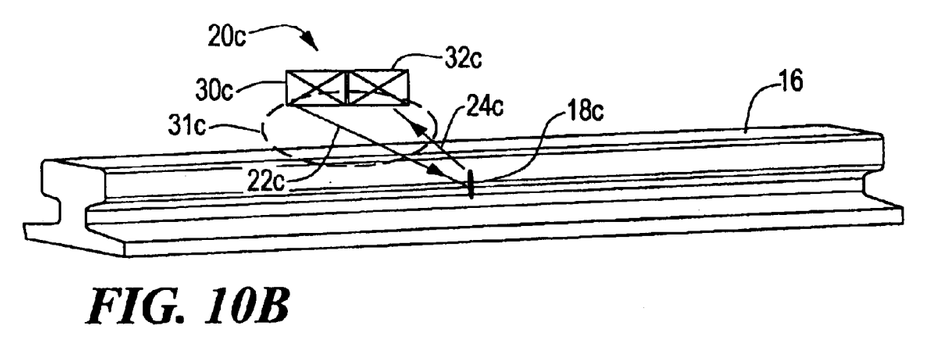
Figure 10C:
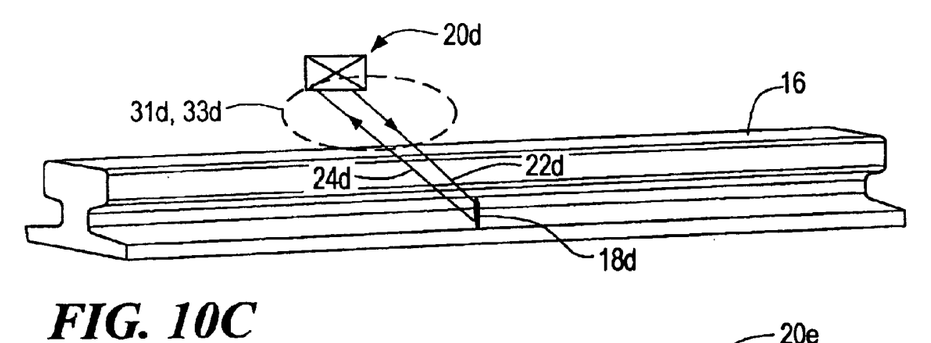

Although as disclosed herein the acoustic signals are continuous wave signals, this is not a necessary limitation of the invention as pulse or spike pulse signals can also be used. For monitoring internal flaws 18b, c, d, FIGS. 10A, 10B and 10C, an electromagnetic acoustic transducer or EMAT may be used. Such a transducer 20b, FIG. 10A, may include an electromagnetic transmitter 30b and receiver 32b for monitoring internal flaws such as flaw 18b. While transmitter and receiver 30b and 32b are spaced apart, FIG. 10A, this is not a necessary limitation for as shown in FIG. 10B, EMAT transmitter 30c and receiver 32c may be adjacent to one another and it is not necessary that the receiver and transmitter be separate, for as shown in FIG. 10C an EMAT transducer 20d which both transmits and receives can be used. As is well known, the EMAT transmitter 30b establishes a varying magnetic field 31b which induces the acoustic signal 22b in rail 16. EMAT receiver 32b through its magnetic field 33b senses the acoustic return signal 24b.

Figure 11:
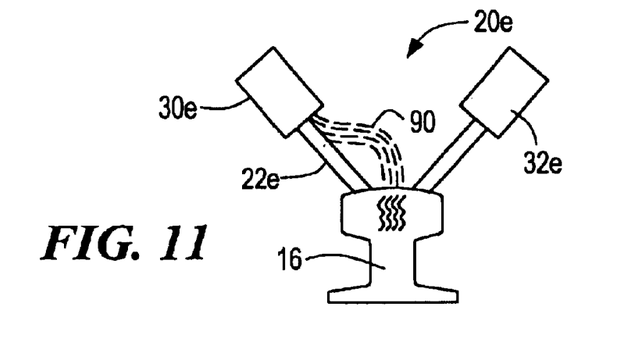
FIG. 11 is a schematic view of another form of transducer using a laser acoustic transmitter.

Yet another transducer 20e, FIG. 11, is shown in which the transmitter may be a laser 30e that either provides its energy directly over beam 22e or through optical fiber cable 90 delivers its energy to rail 16 where it induces an acoustic wave that propagates in rail 16. The laser should be a powerful one such as a Q-switched Nd:YAG laser. The receiver 32e may be an EMAT transducer or an acoustic transducer as already disclosed or may be an interferometer vibrometer device using a Fabry-Perot technique, for example.

Although specific features of this invention are shown in some drawings and not others, this is for convenience only as each feature may be combined with any or all of the other features in accordance with the invention.

Other embodiments will occur to those skilled in the art and are within the following claims:

What is claimed is:

1. A flaw detection system for detecting flaws in a medium using acoustic Doppler effect resulting from relative motion between the medium and the system comprising:

transducer means, spaced from the medium to be inspected, for introducing to and sensing from the medium an acoustic signal that propagates in said medium at a predetermined frequency; and means, responsive to the sensed propagating acoustic signal, for detecting in the sensed acoustic signal the Doppler shifted frequency representative of a flaw in the medium.

2. The flaw detection system using acoustic Doppler effect of claim 1 in which said transducer means includes a separate transmitter and receiver.

3. The flaw detection system using acoustic Doppler effect of claim 1 in which said transducer means is an ultrasonic transducer and said acoustic signal is an ultrasonic signal.

4. The flaw detection system using acoustic Doppler effect of claim 1 in which said transducer transmits an acoustic signal for propagation in said medium.

5. The flaw detection system using acoustic Doppler effect of claim 1 in which said transducer includes an acoustic receiver.

6. The flaw detection system using acoustic Doppler effect of claim 1 in which said means for detecting includes a spectrum analyzer for distinguishing the Doppler effect frequency.

7. The flaw detection system using acoustic Doppler effect of claim 6 in which said means for detecting includes a thresholding circuit for identifying a preselected level as a flaw.

8. The flaw detection system using acoustic Doppler effect of claim 1 in which said means for detecting includes a bandpass filter and a peak detector for distinguishing the Doppler effect frequency.

9. The flaw detection system using acoustic Doppler effect of claim 8 in which said means for detecting includes a thresholding circuit for identifying a preselected level as a flaw.

10. The flaw detection system using acoustic Doppler effect of claim 1 in which said means for detecting includes an A/D converter and a digital filter for distinguishing the Doppler effect frequency, and a thresholding circuit for identifying a preselected level as a flaw.

11. The flaw detection system using acoustic Doppler effect of claim 1 in which said medium is a railroad rail.

12. The flaw detection system using acoustic Doppler effect of claim 1 in which said transducer means transmits to the surface of the medium and receives from the surface of the medium an acoustic signal and the flaws detected are surface flaws.

13. The flaw detection system using acoustic Doppler effect of claim 1 in which said transducer means induces an acoustic signal internally in the medium and the flaws detected are internal flaws.

14. A flaw detection system for detecting flaws in a medium using acoustic Doppler effect resulting from relative motion between the medium and the system comprising:

acoustic transducer means, spaced from the medium to be inspected, for transmitting an acoustic signal to and receiving the reflected acoustic signal at a predetermined frequency from the surface of the medium to be inspected; and means, responsive to the reflected acoustic signal, for distinguishing the Doppler shifted frequency in the reflected acoustic signal from the predetermined frequency of the transmitted acoustic signal representative of a surface flaw in the medium.

15. A flaw detection system for detecting flaws in a medium using acoustic Doppler effect resulting from relative motion between the medium and the system comprising:

transducer means, spaced from the medium to be inspected, for inducing an acoustic signal to propagate in the medium at a predetermined frequency and sensing the propagating acoustic signal in the medium; and means, responsive to the sensed propagating acoustic signal, for distinguishing the Doppler shifted frequency representative of a flaw in the medium.

* * * * *